(12) United States Patent
Mithen et al.

(10) Patent No.: US 6,340,784 B1
(45) Date of Patent: Jan. 22, 2002

(54) METHOD FOR SELECTIVE INCREASE OF THE ANTICARCINOGENIC GLUCOSINOLATES IN BRASSICA SP.

(75) Inventors: Richard Mithen, Norwich; Kathy Faulkner, East Dereham; Gary Williamson, Kings Lynn, all of (GB)

(73) Assignee: Plant Bioscience Limited (GB)

( * ) Notice: Subject to any disclaimer, the term of this patent is extended or adjusted under 35 U.S.C. 154(b) by 0 days.

(21) Appl. No.: 09/288,026

(22) Filed: Apr. 8, 1999

Related U.S. Application Data (60) Provisional application No. 60/081,169, filed on Apr. 9, 1998.

(51) Int. Cl.⁷ .............................. A01H 1/02; A01H 5/00; C12N 5/04
(52) U.S. Cl. ...................... 800/306; 800/269; 800/264; 800/273; 800/267; 800/298; 435/410
(58) Field of Search ................................ 800/260, 265, 800/266, 267, 269, 298, 306, 264, 273; 435/410

(56) References Cited

PUBLICATIONS

Carlson et al. Journal of the American Society of Horticultural Science, vol. 112, pp. 173–178, 1987.*
Fenwick et al. Critical Review of Food Science and Nutrition, vol. 18, pp. 123–201, 1983.*
Giamoustaris et al. Theoretical and Applied Genetics, vol. 93, pp. 1006–1010, 1996.*
Juvick et al. HortScience, vol. 32, abstract 733, 1997.*
Prochaska et al. Proceedings of the National Academy of Science, vol. 89, pp. 2394–2398, 1992.*
Tawfig et al. Theoretical and Applied Genetics, vol. 93, pp. 833–839, 1994.*
L. W. Wattenberg, (1985) "Chemoprevention of Cancer", *Cancer Res.* 45, 1–8.
Y. Zhang, et al (1992) "A major inducer of anticarcinogenic protective enzymes from broccali: Isolatin and elucidation of structure", *Proc. Natl. Acad. Sci. U.S.A.* 89, 2399–2403.
N. Tawfiq, et al (1995) "Dietary glucosinolates as blocking agents against carcinogenesis: glucosinolate breakdown products assessed by induction of quinone reductase activtiy in murine hepalc 1 c7 cells", *Carcinogenesis* 16, 1191–1194.
Y. Zhang, et al (1994) "Anticarcinogenic activities of sulforaphane and structurally related synthetic norbornyl isothiocyanates", *Proc. Natl. Acad. Sci. USA* 91, 3147–3150.
G. Block, et al (1992) "Fruit, Vegetables, and Cancer Prevention: A Review of the Epidemiological Evidence", *Nutr. And Cancer* 18, 1–29.
G. Fenwick, et al (1983) "Glucosinolates and their breakdown products in food and food plants", *Crit. Rev. Food Sci. Nutri,* 18, 123–201.
R. Mithen, et al (1987) "Glucosinolates of wild and cultivated *Brassica* species", *Phytochemistry* 26, 1969–1973.

A. Giamoustaris, et al (1996) "Genetics of aliphatic glucosinolates. IV. Side–chain modification in *Brassica oleracea*", *Theor. Appl. Genet.* 93, 1006–1010.
H.J. Prochaska, et al (1992) "Rapid detection of inducers of enzymes that protect against carcinogens", *Proc. Nat. Acad. Sci. USA*, 89, 2394–2398.
P. Talalay, et al (1988) "Identification of a common chemical signal regulating the induction of enzymes that protect against chemical carcinogenesis", *Proc. Natl. Acad. Sci. USA* 85, 8261–8265.
N. Tawfig, et al (1994) *Exp. J. Cancer Prev.* 3, 285–292.
E. J. R. Bohuon, et al (1996) "Aligment of the conserved C genomes of *Brassica oleracea* and Brassica napus", *Theor. Appl. Genet.* 93, 833–839.
R. Magrath, et al (1993) "The inheritance of aliphatic glucosinolates in *Brassica napus*", *Plant Breeding* 111, 55–72.
H.J. Prochaska et al (1988) "Direct measurement of NAD(P)H: Quinone reductase from cells cultured microtiter wells: A screening assay for anticarcinogenic enzyme inducers", *Anal. Biochem* 169, 328–336.*
G. Williamson, et al (1996) "Dietary quercetin glycosides: antioxidant activity and induction of the anticarcinogenic phase II marker enzyme quinone reductase in Hepalclc 7 cells", *Carcinogenesis* 17, 2385–2387.*
D.Toroser, et al, (1995) "RFLP mapping of quantitative trait loci controlling seed aliphatic–glucosinolate content in oilseed rape (*Brassica napus* L.)", *Theor Appl Genet* 91:802–808.*
M.E. Ferreira, et al, (1994) "RFLP mapping of *Brassica napus* using doubled haploid lines", *Theor Appl Genet* 89:615–621.*

(List continued on next page.)

*Primary Examiner*—Gary Benzion
*Assistant Examiner*—David H Kruse
(74) *Attorney, Agent, or Firm*—Lorusso & Loud (57) ABSTRACT

The invention relates to a method for producing *Brassica oleracea* with elevated anticarcinogenic glucosinolate derivatives. The elevated levels are obtained by crossing wild *Brassica oleracea* species with *Brassica oleracea* breeding lines, and subsequently selecting hybrids with levels of 4-methylsulfinylbutyl and/or 3-methylsulfinylpropyl glucosinolates elevated above that initially found in *Brassica oleracea* breeding lines. The invention also relates to edible Brassica plants, such as broccoli plants, with elevated levels of 4-methylaulfinylbutyl glucosinolate and/or 3-methylsulfinylpropyl glucosinolates, and to seeds of such plants.

19 Claims, 3 Drawing Sheets

OTHER PUBLICATIONS

J.A. Scheffler, et al (1994) "Opportunities for gene transfer from transgenic oilseed rape (*Brassica napus*) to related species", *Transgenic Research* 3, 263–278.*

Kushad, Mosbah M.; Brown, Allan F.; Kurilich, Anne C.; Juvik, John A.; Klein, Barbara P.; Wallig, Mathew A.; and Jeffery, Elizabeth H., "Variation of Glucosinolates in Vegetable Crops of *Brassica oleracea*", 1999, p. 1541–1548, J. Agric. Food Chem., 47.

European Journal of Cancer Prevention, vol. 3, 1994, pp. 285–292.

J.W. Fahey, et al (1997) "Broccoli sprouts: An exceptionally rich source of inducers of enzymes that protect against chemical carcinogens", *Proc. Natl. Acad. Sci. U.S.A.* vol. 94, 10367–10372.

D.G. Carlson, et al (1987) "Glucosinolates in Crucifer Vegatables: Broccoli, Brussels Sprouts, Cauliflower, Collards, Kale, Mustard Greens, and Kohlrabi", *J. Amer. Soc. Hort. Sci.* 112(1):173–178.

* cited by examiner

METHOD FOR SELECTIVE INCREASE OF THE ANTICARCINOGENIC GLUCOSINOLATES IN *BRASSICA SP.*

This application claims priority under 35 U.S.C. 119(e) to Provisional Application No. 60/081,169, filed Apr. 9, 1998, the teachings of which are incorporated herein by reference.

FIELD OF INVENTION

The present invention relates to methods for the selective increase of anticarcinogenic glucosinolate derivatives in Brassica species, and to Brassica species with enhanced levels of anticarcinogenic glucosinolate derivatives and in particular edible Brassica vegetables with elevated levels of the anticarcinogenic glucosinolate derivatives 4-methylsulfinylbutyl isothiocyanate and/or 3-methylsulfinylpropyl isothiocyanate. The present invention also provides methods for selection of genetic combinations of broccoli containing high levels of anticarcinogenic glucosinolate derivatives and methods to evaluate the anticarcinogenic properties of these genetic combinations. The invention further relates to compositions of matter comprising Brassica vegetables with concentrations of 4-methylsulfinylbutyl glucosinolate and/or 3-methylsulfinylpropyl glucosinolate between 10 and 100 μmoles/g dry weight.

BACKGROUND ART

The present invention provides methods for the production of Brassica vegetables with elevated levels of specific glucosinolates and derivatives thereof. In particular the invention provides methods for the production and selection of Brassica vegetables with elevated levels of 3-methylsulfinylpropyl and/or 4-methylsulfinylbutyl glucosinolates. These glucosinolates are converted by the activity of the enzyme myrosinase into isothiocyanate derivatives which have been demonstrated to be potent inducers of phase II detoxification enzymes, elevated activity of which is associated with reduced susceptibility to the neoplastic effects of carcinogens. The invention provides genetic combinations which 1.) exhibit elevated levels of 4-methylsulfinylbutyl glucosinolate and/or 3-methylsulfinylpropyl glucosinolate and 2.) exhibit low activity of the GSL-ALK allele which encodes an activity capable of converting these glucosinolates into the alkenyl derivatives, which do not posses the anti-carcinogenic properties of the isothiocyanate derivatives of these glucosinolates and 3.) suitable myrosinase activity capable of producing isothiocyanate derivatives of said glucosinolates. Accordingly these genetic combinations provide elevated levels of specific glucosinolates, reduced production of alkenyl derivatives of these glucosinolates and favoured production of isothiocyanate derivatives of said glucosinolates. The invention further relates to the use of genetic markers to select the genetic combinations described above.

It is known that a diet high in vegetables is associated with a reduction in the risk of certain types of cancer and hence it is desirable to include a significant amount of vegetables in the human diet. The anticarcinogenic activity of vegetables has been associated with the presence of several classes of secondary metabolites. Evidence is growing that some of these secondary metabolites are involved in lowering the risk of certain types of cancer and hence are considered anticarcinogenic. Accordingly, enhancing the level of anticarcinogenic metabolites provides a useful strategy for the reduction of cancer risk, in complementation with dietary advice to increase the consumption of vegetables.

The precise mechanism by which vegetables provide a decreased risk of many types of cancer is not known with certainty, but there are many lines of evidence which support the involvement of vegetables in the prevention of cancer. In particular, the role of cruciferous vegetables in the prevention of cancer is widely supported through epidemiological studies and more recently biochemical studies. One class of secondary metabolites that is implicated in the beneficial effects of cruciferous vegetables is the isothiocyanate derivatives of certain glucosinolates. Four complementary pieces of evidence suggest that isothiocyanates derived from the hydrolysis of methylsulfinylalkyl glucosinolates found in crucifers may be important in the human diet in reducing the risk of cancer. (1.) Dietary provision of cruciferous vegetables protects rodents against chemically induced cancer (Wattenberg, L. W. (1985) *Cancer Res.* 45, 1–8.). (2.) Methylaulfinylalkyl isothiocyanates are known to be potent inducers of phase II detoxification enzymes in murine hepatoma Hepa 1c1c7 cells in culture (Zhang, Y., Talalay, P., Cho, C.-G., & Posner, G. H. (1992) *Proc. Natl. Acad. Sci. USA* 89, 2399–2403 and Tawfiq, N., Heaney, R. K., Plumb, J. A., Fenwick, G. R., Musk, S. R. R., & Williamson, G. (1995) *Carcinogenesis* 16, 1191–1194.), which are associated with reduced susceptibility of mammals and mammalian cell cultures to the toxic and neoplastic effects of carcinogens. (3.) Sulforaphane (4-methylsulfinylbutyl isothiocyanate) blocks the formation of mammary tumors in Sprague-Dawley rats treated with 9,10-dimethyl-1,2-benzanthracene (Zhang, Y., Kensler, T. W., Cho, C.-G., Posner, G. H., & Talalay, P. (1994) *Proc. Natl. Acad. Sci. USA* 91, 3147–3150.). (4.) Epidemiological studies show that people with high levels of vegetables in their diet are less susceptible to cancer (Block, G., Patterson, B., & Suber, A. (1992) *Nutr. and Cancer* 18, 1–19.). Thus the beneficial effects of a diet high in certain glucosinolates may included a reduction in the risk of cancer. However, it appears that only certain glucosinolates and more accurately, certain derivatives of specific glucosinolates may be primarily responsible for the beneficial effect.

There are numerous individual glucosinolates in cruciferous plants. Glucosinolates have a common glycone moiety and a variable aglycone side chain. The structure of the glucosinolate side chain varies in length and chemical composition.

Glucosinolates are formed by the action of a number of enzymes, encoded by a small number of glucosinolate biosynthetic alleles (GSL alleles). In the glucosinolate pathway, methionine is converted to homo-methionine and dihomo-methionine by the activity of the GSL-ELONG allele. Homo-methionine is eventually converted to 3-methylthiopropyl glucosinolate followed by conversion to 3-methylaulfinylpropyl glucosinolate by the activity of GSL-OXID allele and finally 2-propenyl glucosinolate by the activity of GSL-ALK allele. Dihomo-methionine is converted to 4-methylthiobutyl glucosinolate, then to 4 methylsulfinylbutyl glucosinolate by the activity of GSL-OXID allele, then to 3-butenyl glucosinolate by the activity of GSL-ALK allele and finally converted to 2-hydroxy-3-butenyl glucosinolate by the activity of GSL-OH allele.

In general, the 3-methylsulfinylpropyl glucosinolates and 4-methylthiobutyl glucosinolates produce non-volatile isothiocyanates and hence these particular glucosinolates contribute little to flavour. In contrast, the volatile alkenyl derivatives can contribute to flavour, both positively and negatively, dependant on the plant species and particular glucosinolate derivative.

In *B. oleracea* vegetables, glucosinolates have either a three or four carbon side chain. Glucosinolates can be hydrolysed by the action of myrosinase which is often induced upon tissue damage. Many vegetables have alkenyl (2-propenyl and 3-butenyl) glucosinolates which result in the production of volatile products upon hydrolysis through the action of myrosinase. Some vegetables contain a 2-hydroxy-3-butenyl glucosinolate called progoitrin. This glucosinolate produces an unstable isothiocyanate that spontaneously cyclizes to produce oxazolidone-2-thiones, which are undesirable in diets due to their goitrogenic properties. Isothiocyanates derived from alkenyl and hydroxyalkenyl glucosinolates can have both positive and negative effects on flavour.

Broccoli accumulates low levels of glucosinolates with 4-metylsulfinylbutyl and 3-methylsulfinylpropyl side chains since broccoli has a greatly reduced activity of the GSL-ALK allele, responsible for the conversion of glucosinolates into alkenyl derivatives. It is believed that the popularity of broccoli as a vegetable is due in part to the relatively modest contribution to taste made by 4-metylsultinylbutyl and 3-methylsulfinylpropyl glucosinolate derivatives in contrast to the strong flavour imparted by other glucosinolates, particularly the volatile derivatives of glucosinolates.

Thus, methods to increase the dietary amount of specific isothiocyanate derivatives of certain glucosinolates may provide vegetables with enhanced anticarcinogenic properties without altering the taste and/or palatability of the vegetable. However, the art does not provide a means to conveniently increase the levels of the specific glucosinolates in cruciferous vegetables. Moreover, the art does not provide a convenient means to assure that these glucosinolates are not converted to the alkenyl derivatives, but rather the isothiocyanate derivatives which have anticarcinogenic properties. Of the numerous glucosinolates that may be produced by Brassica vegetables, 4-methylsulfinylbutyl glucosinolate and 3-methylsulfinylpropyl glucosinolate have been identified as being the precursors to the most potent anticarcinogenic isothiocyanate derivatives. The art does not provide a convenient means to increase these specific glucosinolates in a specific fashion while preventing the formation of other glucosinolate or glucosinolate derivatives that may have undesirable flavour characteristics.

4-Methylsulfinylbutyl glucosinolate and 3-methylsulfinylpropyl glucosinolate glucosinolates are found in several cruciferous vegetables, but are most abundant in broccoli varieties (syn. calabrese: *Brassica oleracea* L. var. italica) which lack a functional allele at the GSL-ALK locus. The presence of a functional GSL-ALK allele converts these glucosinolates to their alkenyl homologues, which are poor inducers of phase II enzymes (Tawfiq, N., Heaney, R. K., Plumb, J. A., Fenwick, G. R., Musk, S. R. R., & Williamson, G. (1995) *Carcinogenesis* 16, 1191–1194.). Therefore the presence of a functional GSL-ALK allele precludes the possibility of producing a variety with high levels of these anticarcinogenic isothiocyanates since the glucosinolates will be converted to alkenyl derivatives. Additionally the production of isothiocyanates from glucosinolates requires the activity of the enzyme myrosinase. Hence enhanced production of these specific isothiocyanates depends on both the levels of glucosinolate precursors (which are influenced by the activity encoded by the GSL-ALK allele) and the levels or activity of myrosinase which produces the isothiocyanate derivatives of glucosinolates.

Accordingly a genetic combination which specifies the production of high levels of 4-methylsulfinylbutyl glucosinolate and/or 3-methylsulfinylpropyl glucosinolates is desirable, but the production of the anticarcinogenic isothiocyanate derivatives of these glucosinolates requires additional genetic combinations. Thus methods to achieve these genetic compositions provides novel compositions of matter not presently found in commercially grown cruciferous vegetables. The present invention recites methods for achieving these genetic combinations.

The levels of glucosinolates in commercially grown broccoli are relatively low compared to those found in salad crops such as rocket (*Eruca sativa*), which accumulates 4-methylthiobutyl glucosinolate, and watercress (*Rorippa nasturtium-aquaticum*) which accumulates phenethyl glucosinolate (Fenwick, G. R., Heaney, R. K., & Mullin, W. J. (1983) *Crit. Rev. Food Sci. Nutr.* 18, 123–201). Exposure to enhanced levels of 4-methylsulfinylbutyl glucosinolate and/or 3-methylsulfinylpropyl glucosinolate in broccoli would be expected to enhance the potency of induction of phase II enzymes when ingested. Thus broccoli with increased levels of the anticarcinogenic 4-methylsulfinylbutyl isothiocyanate and/or 3-methylsulfinylpropyl isothiocyanate would be a valuable addition to a diet that is designed to lower the risk of cancer. Additionally, such changes would be unlikely to lead to reduced palatability as methylsulfinylalkyl glucosinolates are non-volatile and have a relatively small contribution to flavour, in contrast to the majority of other isothiocyanates found in vegetables and salad crops (Fenwick, G. R., Heaney, R. K., & Mullin, W. J. (1983) *Crit. Rev. Food Sci. Nutr.* 18, 123–201). Thus altering the levels of these specific glucosinolates would not change the taste of the cruciferous vegetables which carry the genetic combinations encoding the trait.

Many wild members of the *Brassica oleracea* species complex (chromosome number, n=9) have high levels of individual aliphatic glucosinolates (Mithen, R., Lewis, B. G., & Fenwick, G. R. (1987) *Phytochemistry* 26, 1969–1973. and Giamoustaris, A. & Mithen, R. (1996) *Theor. Appl. Genet.* 93, 1006–1010.). Studies on the genetics of glucosinolates in these taxa has been instrumental in elucidating the genetic pathway for glucosinolate biosynthesis. It is evident that certain species in this taxa could be valuable in Brassica breeding programs designed to specifically enhance 4-methylsulfinylbutyl glucosinolate and/or 3-methylsulfinylpropyl glucosinolate and, by so doing, the anticarcinogenic potential of the plant. However, the art does not provide methods to increase the concentration of 4-methylsulfinylbutyl glucosinolate and/or 3-methylsulfinylpropyl glucosinolate through genetic combinations nor does it provide a convenient means by which the anticarcinogenic properties of the vegetables containing said genetic combinations can be assessed. The present invention provides these methods and genetic combinations.

Foremost amongst these are genetic combinations which incorporate the genes from members of the *B. villosa-rupestris* complex from Sicily, which possess a non-functional GSL-ALK allele, and may be the wild progenitors of cultivated broccoli. Thus the present invention utilizes wild relatives and progenitors of commercial broccoli as a source of the genes needed to derive a genetic combination capable of producing high levels of 4-methylsulfinylbutyl and/or 3-methylsulfinylpropyl glucosinolates and the genetic combination that favours the production of isothiocyanate derivatives of these glucosinolates rather than alkenyl derivatives.

4-Methylsulfinylbutyl isothiocyanate (also referred to as sulforaphane), derived from the corresponding glucosinolate found in some Brassica species, has previously been identified as a potent inducer of phase II detoxification enzymes (e.g. QR; quinone reductase [NADP(H):quinone-acceptor] oxidoreductase) in murine hepatoma Hepa 1c1c7 cells. Similarly, 3-methylsulfinylpropyl isothiocyanate is a strong inducer of phase II enzymes. Measurement of the induction of QR in murine hepatoma Hepa 1c1c7 cells provides a rapid and reliable indicator of the ability of vegetable extracts to induce phase II enzymes in mammalian cells (Prochaska, H. J., Santamaria, A. B., & Talalay, P. (1992) *Proc. Natl. Acad. Sci. USA* 89, 2394–2398.), and hence of putative anticarcinogenic activity. This assay has been used to assess the potential of synthetic isothiocyanates (Zhang, Y., Talalay, P., Cho, C.-G., & Posner, G. H. (1992) *Proc. Natl. Acad. Sci. USA* 89, 2399–2403 and Talalay, P., De Long, M. J., & Prochaska, H. J. (1988) *Proc. Natl. Acad. Sci. USA* 85, 8261–8265.), extracts from cruciferous vegetables (Tawfiq, N., Wanigatunga, S., Heaney, R. K., Musk, S. R. R., Williamson, G., & Fenwick, G. R. (1994) *Exp. J. Cancer Prev.* 3, 285–292.) and myrosinase-treated glucosinolates (Tawfiq, N., Heaney, R. K., Plumb, J. A., Fenwick, G. R., Musk, S. R. R., & Williamson, G. (1995) *Carcinogenesis* 16, 1191–1194). However, the glucosinolate/isothiocyanate content of the vegetable extracts has generally not been reported nor has the relative anticarcinogenic potential of various cruciferous vegetables been reported.

In the present invention, this assay has been used to determine the relationship between the ability to induce QR activity (anticarcinogenic potential) and the glucosinolate, content of three wild members of the *B. oleracea* complex, which have high levels of 3-methylthiopropyl (*B. drepanensis*) 3-methylsulfinylpropyl (*B. villosa*) and 2-propenyl (*B. atlantica*) glucosinolates respectively, when combined with commercial broccoli cultivars through conventional crosses and hybrids between the wild accessions and a commercial double haploid broccoli breeding lines. Accordingly methods and compositions have been derived which identify the genetic compositions required for the stable production of specific glucosinolates (e.g. of 4-methylsulfinylbutyl and/or 3-methylsulfinylpropyl glucosinolates) and the production of the corresponding isothiocyanate derivatives. These genetic combinations provide useful breeding lines for the production of commercial varieties of broccoli and other cruciferous vegetables that have 10–100 times the levels of these anticarcinogenic compounds than currently found in commercially grown varieties.

It has been found for example, that a ten-fold increase in the level of 4-methylsulfinylbutyl glucosinolate is obtained by crossing broccoli cultivars with selected wild taxa of the *Brassica oleracea* (chromosome number, n=9) complex. Similarly increases in levels of 3-methylsulfinylpropyl glucosinolate is observed. Tissue from these hybrids exhibited a 100-fold increase in the ability to induce quinone reductase in Hepa 1c1c7 cells over commercially grown broccoli cultivars due to both an increase in 4-methylsulfinylbutyl and/or 3-methylsulfinylpropyl glucosinolates and the increased conversion of 4-methylsulfinylbutyl glucosinolate to sulforaphane. Accordingly the invention provides methods and genetic compositions for the production of commercially valuable cruciferous vegetables containing high levels of anticarcinogenic secondary metabolites. The invention further contemplates the development of broccoli breeding lines with enhanced anticarcinogenic activity.

The selection of breeding lines with high levels of anticarcinogenic compounds is further facilitated by the use of molecular markers to establish the chromosomal location of the glucosinolate biosynthetic genes and to assist in selection of backcross lines which contain the genetic composition of greatest utility for the purposes of enhancing the levels of anticarcinogenic compounds in broccoli.

SUMMARY OF THE INVENTION

The present invention provides methods to increase levels of 4-methylsulfinylbutyl and/or 3-methylsulfinylpropyl glucosinolates in Brassica vegetables by genetic means. These means include crossing of wild Brassica species to broccoli species, selection of lines with elevated 4-methylaulfinylbutyl and/or 3-methylaulfinylpropyl glucosinolates and evaluating the anticarcinogenic properties of said genetic combinations by measuring the potency of plant cell extracts to induce phase II enzymes. RPLP markers can be used to select lines in crosses which have a high proportion of broccoli genetic background and to establish the position of the relevant glucosinolate biosynthesis genes on the map of the Brassica genome.

Hybrids between commercial broccoli cultivars and the two wild species *B. villosa* and *B. drepanensis* are fully fertile and backcross populations are made. Broccoli lines with enhanced levels of 4-methylsulfinylbutyl and/or 3-methylsulfinylpropyl glucosinolates and associated anticarcinogenic activity are developed from these populations. The efficiency of the development of these lines is considerably enhanced by the availability of molecular markers to select for both glucosinolate content and the desired genetic background.

DETAILED DESCRIPTION OF THE INVENTION

It is an object of the present invention to provide an edible cruciferous vegetable with high levels of anticarcinogenic compounds, namely 4-methylsulfinylbutyl isothiocyanate and/or 3-methylsulfinylpropyl isothiocyanate.

It is another object of the present invention to provide methods for the selective increase of anticarcinogenic glucosinolate derivatives in Brassica species, and to provide Brassica species with enhanced levels of anticarcinogenic glucosinolate derivatives and in particular edible Brassica vegetables with elevated levels of the anticarcinogenic glucosinolate derivatives 4-methylsulfinylbutyl isothiocyanate and/or 3-methylsulfinylpropyl isothiocyanate.

It is yet another object of the present invention to provide methods for selection of genetic combinations of broccoli containing high levels of anticarcinogenic glucosinolate derivatives and methods to evaluate the anticarcinogenic properties of these genetic combinations.

It is still another object of the present invention to provide compositions of matter comprising Brassica vegetables with concentrations of 4-methylsulfinylbutyl and/or 3-methylsulfinylpropyl glucosinolates between 10 and 100 µmoles/g dry weight.

Figure 1:
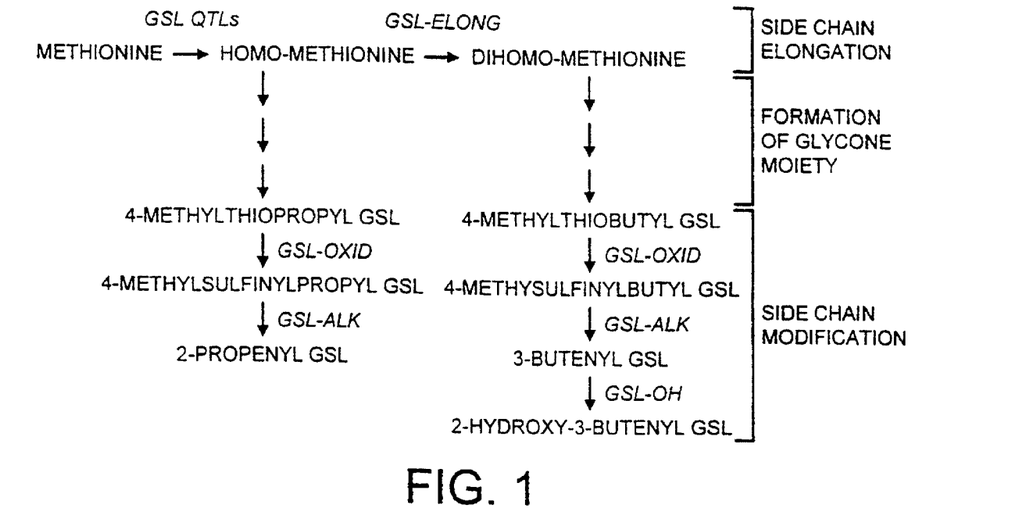
FIG. 1. Genetic model of aliphatic glucosinolate biosynthesis in Brassica.

These and other objects of the invention are provided by one or more of the embodiments described below, The selection of broccoli with elevated levels off anticarcinogenic glucosinolates is not possible in the present commercial genetic background used to develop commercial broccoli cultivars. Based on the genetic model of glucosinolate biosynthesis shown in FIG. 1, the production of 4-methylsulfinylbutyl and/or 3-methylsulfinylpropyl glucosinolates is dependant on a number of genetic factors. These include low activity of the GSL-ALK allele and proper levels of activity encoded by the GSL-OXID alleles and other alleles responsible for the production of glucosinolate precursors. It is believed that the relatively mild taste of broccoli is associated with relatively low levels of glucosinolates in general and low levels of volatile glucosinolates in particular. This is evident when the total glucosinolate profiles of commercial broccoli and wild relatives are compared.

Thus methods to derive broccoli with desirable flavour characteristics and elevated levels of anticarcinogenic glucosinolates must encompass selection of lines with the proper genetic combination which do not produce strong flavoured alkenyl glucosinolates. It is also desirable to maintain low levels of other glucosinolates in order to avoid off-flavour production. Thus methods to achieve the specific elevation of 4-methylsulfinylbutyl and/or 3-methylsulfinylpropyl glucosinolates must not lead to an overall production of glucosinolates or production of alkeynl glucosinolates. The present invention provides methods to accomplish these goals.

Under normal field conditions, it is believed that wild type *B. oleracea* would not likely cross-fertilize with cultivated *B. oleracea*. It is thought that compatibility traits are turned off when the cultivars flower.

The present invention also contemplates the use of genetic markers to facilitate the selection of lines which contain the desired genetic combination. The use of RFLP markers, or DNA probes which segregate with specific traits is well known in the art, however the present invention describes specific DNA probes that have been shown to be useful for the selection of genetic combinations that lead to elevated levels of 4-methylsulfinylbutyl and/or 3-methylsulfinylpropyl glucosinolates in *Brassica oleracea*. Furthermore, RFLP analysis provides a useful means to assess the portion of the genome of a hybrid plant which is derived from broccoli or wild species. Thus the use of RPLP or DNA probes finds utility in the rapid selection of plants which contain the desired proportion of wild species and broccoli genomes. Thus selection of broccoli with elevated levels of 4-methylsulfinylbutyl and/or 3-methylsulfinylpropyl glucosinolates comprising a high percentage of the desired commercial genome is greatly facilitated by the use of DNA markers to analyse hybrid plants following crossing of broccoli with wild species.

The present invention also describes methods for the assessment of the anticarcinogenic properties of broccoli containing elevated levels of 4-methylsulfinylbutyl and/or 3-methylsulfinylpropyl glucosinolates through assays for the induction of phase II enzymes. Although the long-term anticarcinogenic effects of specific derivatives of 4-methylsulfinylbutyl and/or 3-methylsulfinylpropyl glucosinolates can not be precisely determined and will be further dependent on many additional factors, dietary and otherwise, the use of the induction assay provides compelling evidence for the anticarcinogenic effects of the isothiocyanate derivatives of the specific glucosinolates.

Thus the present invention describes methods that permit the selection of Brassica sp. with elevated levels of 4-methylsulfinylbutyl and/or 3-methylsulfinylpropyl glucosinolates, methods to evaluate the anticarcinogenic effects of said plant species, and methods and compositions that permit the derivation of broccoli lines with anticarcinogenic properties.

In one embodiment of the present invention, a method is used to select broccoli lines with elevated levels of specific glucosinolates which comprises:

I.) Crossing wild species with broccoli double haploid breeding lines;

II.) Analyzing F1 hybrids, selecting the hybrids with the highest level of 4-methylsulfinylbutyl and/or 3-methylsulfinylpropyl glucosinolates and backcrossing to broccoli breeding lines;

III.) Analysis of glucosinolates in individual plants of the B1 (Backcross 1) generation;

IV.) One or two further rounds of backcrossing (B2, B3) with selection of plants with the highest level of 4-methylaulfinylbutyl and/or 3-methylsulfinylpropyl glucosinolates, anticarcinogenesis screening of selected individuals by induction of phase II enzymes;

V.) Analysis of B3 (Backcross 3) population with selection of plants with the highest level of 4-methylsulfinylbutyl and/or 3-methylsulfinylpropyl glucosinolates, anticarcinogenesis screening of selected individuals by induction of phase II enzymes;

VI.) Selection of a broccoli line with elevated levels of 4-methylsulfinylbutyl and/or 3-methylsulfinylpropyl glucosinolates which carries the anticarcinogenic trait capable of causing a strong induction of phase II enzymes.

Thus the method allows for the selection of broccoli lines with elevated levels of 4-methylsulfinylbutyl and/or 3-methylsulfinylpropyl glucosinolates. The elevated levels of these specific glucosinolates is correlated with the anticarcinogenic property by evaluation of the induction of phase II enzymes. By employing backcrossing, genetic combinations are derived which comprise the anticarcinogenic trait in a genetic background found in commercial broccoli. Accordingly the production of 4-methylsulfinylbutyl and/or 3-methylsulfinylpropyl glucosinolates in commercial cultivars of broccoli is accomplished, giving rise to a new and valuable broccoli composition.

In another embodiment of the present invention, the anticarcinogenic capability of the lines is further combined with specific alleles for self incompatibility which is useful in seed production strategies. It is known that certain cruciferous species carry various alleles for self-incompatibility and these alleles are often employed for hybrid seed production. Thus hybrid broccoli may be produced which carries the genetic combination that produces elevated levels of 4-methylsulfinylbutyl and/or 3-methylaulfinylpropyl glucosinolates. It is another object of the present invention to select broccoli lines with high levels of 4-methylsulfinylbutyl and/or 3-methylsulfinylpropyl glucosinolates and a specific combination of self-incompatibility (SI) alleles. In some instances, it may be possible to use a molecular probe for identification of SI alleles, such as the probe pW150 (available from Dr. Tom Osborne, Department of Agronomy, University of Wisconsin, Madison, Wis., 53706 and described in Toroser et al., Theoretical and Applied Genetics, 91:802–808.1995), or analysis of the actual SI protein can provide selection of the desired SI allele.

Thus in another embodiment of the present invention, a method is used to select broccoli lines with high levels of specific glucosinolates and SI alleles which comprises:

I.) Crossing wild species with broccoli double haploid breeding lines containing specific SI alleles;

II.) Analyzing F1 hybrids, selecting the hybrids with the highest level of 4-methylsulfinylbutyl and/or 3-methylaulfinylpropyl glucosinolates and backcrossing to broccoli breeding lines, screening for SI alleles with RFLP markers, selection of individuals with desired combination of contrasting SI alleles;

III.) Analysis of glucosinolates in individual plants of the B1 (Backcross 1) generation;

IV.) One or two further rounds of backcrossing with selection of plants with the highest level of 4-methylsulfinylbutyl and/or 3-methylsulfinylpropyl glucosinolates, screening for proper SI alleles with RFLP markers, anticarcinogenesis screening of selected individuals by induction of phase II enzymes;

V.) Analysis of B3 (Backcross 3) population with selection of plants with the highest level of 4-methylsulfinylbutyl and/or 3-methylsulfinylpropyl glucosinolates, anticarcinogenesis screening of selected individuals by induction of phase II enzymes;

VI.) Selection of a broccoli line with elevated levels of 4-methylsulfinylbutyl and/or 3-methylsulfinylpropyl glucosinolates and proper SI alleles which carries the anticarcinogenic trait capable of causing a strong induction of phase II enzymes.

Thus broccoli lines are derived which carry specific SI alleles useful for crossing in a hybrid seed production scheme. Accordingly hybrid broccoli seed that carries the genetic combination for elevated levels of 4-methylsulfinylbutyl and/or 3-methylsulfinylpropyl glucosinolates can be produced by crossing with the appropriate parent. Said seed is valuable since hybrid broccoli also carries many genetic combinations important for agronomic performance.

As another embodiment of the present invention, a method is described which employs the use of DNA markers that segregate with specific glucosinolate profiles. In this method, the use of DNA markers, or more specifically markers known as QTLs (quantitative trait loci) are used Lo select the genetic combination in broccoli that leads to elevated levels of 4-methylsulfinylbutyl and/or 3-methylsulfinylpropyl glucosinolates. In particular the use of the markers known as pW176, pW207 and pW141 located on chromosome 2 and the markers known as pW224, pW114, pW145, pW123, pW138, pW197, pW229, pW106 located on chromosome 5 is described (available from Dr. Tom Osborne, Department of Agronomy, University of Wisconsin, Madison, Wis., 53706 and described in Toroser et al., Theoretical and Applied Genetics, 91:802–808, 1995 and described in Ferreira et al., Theoretical and Applied Genetics 89:615–621, 1994.)

It has been found that two regions of the genome (found on chromosome 2 and 5) of wild Brassica oleracea are required for the expression of elevated levels of 4-methylsulfinylbutyl and/or 3-methylsulfinylpropyl glucosinolates. The use of the markers greatly facilitates the selection of lines from hybrids and backcross between broccoli and wild species which contain the genetic combination responsible for the production of elevated levels of 4-methylsulfinylbutyl and/or 3-methylsulfinylpropyl glucosinolates. Furthermore, it has been found that the QTL located on chromosome 5 specifically regulates the levels of 3-methysulfinylpropyl glucosinolate and has little effect on the levels of 4-methylsulfinylbutyl glucosinolate. Thus it is possible to manipulate the levels of 3-methysulfinylpropyl glucosinolate and 4-methylsulfinylbutyl glucosinolate independently by the use of molecular probes in addition to simple selection of lines.

Accordingly in this embodiment of the present invention a method to produce broccoli with elevated levels of 4-methylsulfinylbutyl and/or 3-methylaulfinylpropyl glucosinolates is described which comprises:

I.) Crossing wild species with broccoli double haploid breeding lines;

II.) Analyzing F1 hybrids and selecting the hybrids with the highest level of 4-methylsulfinylbutyl and/or 3-methylsulfinylpropyl glucosinolates by screening with RFLP probes associated with the production of 4-methylsulfinylbutyl and/or 3-methylsulfinylpropyl glucosinolates and backcrossing selected lines to broccoli breeding lines;

III.) Analysis of glucosinolates in individual plants of the B1 (Backcross 1) generation;

IV.) One or two further rounds of backcrossing with selection of plants with the highest level of 4-methylsulfinylbutyl and/or 3-methylsulfinylpropyl glucosinolates by screening with RFLP probes associated with the production of 4-methylsulfinylbutyl and/or 3-methylsulfinylpropyl glucosinolates, anticarcinogenesis screening of selected individuals by induction of phase II enzymes;

V.) Analysis of B3 (Backcross 3) population with selection of plants with the highest level of 4-methylsulfinylbutyl and/or 3-methylsulfinylpropyl glucosinolates by screening with RFLP probes associated with the production of 4-methylsulfinylbutyl and/or 3-methylsulfinylpropyl glucosinolates and analysis of glucosinolate profiles, anticarcinogenesis screening of selected individuals by induction of phase II enzymes;

VI.) Selection of a broccoli line with elevated levels of 4-methylsulfinylbutyl and/or 3-methylsulfinylpropyl glucosinolates which carries the anticarcinogenic trait capable of causing a strong induction of phase II enzymes.

Thus the use of RFLP probes for identifying specific regions of the wild Brassica oleracea genome (e.g. so-called QTLs) responsible for the production of elevated levels of 4-methylsulfinylbutyl and/or 3-methylsulfinylpropyl glucosinolates greatly facilitates the production of edible broccoli with anticarcinogenic properties.

The foregoing embodiments allow for the selection of broccoli lines with elevated levels of 4-methylsulfinylbutyl and/or 3-methylsulfinylpropyl glucosinolates, preferably broccoli with a composition comprising concentrations of 4-methylsulfinylbutyl and/or 3-methylsulfinylpropyl glucosinolates between 10 and 100 μmoles/g dry weight. Furthermore, the foregoing embodiments allow for the selection of broccoli lines with elevated levels of 4-methylsulfinylbutyl and/or 3-methylaulfinylpropyl glucosinolates capable of causing a 10–100 fold increase in the induction of phase II enzymes when compared to broccoli cultivars commonly found in commerce.

The skilled artisan would contemplate that the methods described herein may also be applied to obtain cruciferous B. Oleracea vegetables other than broccoli, including cabbage such as white cabbage, green cabbage such as Savoy, cauliflower, Brussels sprouts, kale, kohlrabi and the like. It is further contemplated that rutabaga (B. napus) and turnip (B. rapa) may also be manipulated according to the method and genetic combinations of the present invention.

The following examples illustrate the method but in no way limit the scope of the invention.

EXAMPLE 1

Methods for the Measurement of Glucosinolate Content in Wild and Commercial Brassica Species and Hybrids Thereof A double haploid broccoli breeding line derived from the cultivar Green Duke (referred to as GD DH, Bouhuon, E. J. R., Keith, D. J., Parkin, I. A. P., Sharpe, A. G., & Lydiate, D. J. (1996) Theor. Appl. Genet. 93, 833–839.), three commercial cultivate (Trixie, Green Comet and Marathon) and three wild Brassica species: B. drepanensis Caruel (syn. B. villosa Biv. subsp drepanensis), B. villosa Biv. and B. atlantica (Coss.) O. E. Schultz, were grown in a glasshouse under standard conditions as previously described (Magrath, R., Herron, C., Giamoustaris, A., & Mithen, R. (1993) Plant Breed. 111, 55–72). Each of the wild species was crossed to the GD DH breeding line, $F_1$ seeds were obtained and grown under standard conditions. A deposit of seeds of the cultivar derivative GD DH was made on Feb. 11, 1999 with the National Collection of Industrial and Marine Bacteria Limited (NCIMB) in Aberdeen, Scotland, and was assigned the deposit No. NCIMB 41008. Inflorescences were harvested from the cultivars after 8–12 weeks and from the hybrids after 12–16 weeks, immediately frozen in liquid nitrogen and freeze-dried. Synthetic sulforaphane was kindly supplied by Professor P. Talalay, The John Hopkins University School of Medicine, Baltimore, Md.

Glucosinolates were extracted from the freeze-dried material, converted to desulfoglucosinolates and analysed by HPLC as previously described (Magrath, R., Herron, C., Giamoustaris, A., & Mithen, R. (1993) Plant Breed. 111, 55–72) using benzyl glucosinolate as an internal standard.

Extracts from the freeze-dried material were assessed for their induction activity in murine hepatoma Hepa 1c1c7 cells. Approximately 0.1 g of milled freeze-dried material was moistened by addition of water (2 ml), homogenised and left at room temperature for 1 hr with occasional mixing. Hot 70% (v/v) methanol (3 ml) was added and mixed thoroughly prior to incubation for 15 min at +70° C. The homogenates were cooled to room temperature and centrifuged for 5 min at 3000 r.p.m. Supernatants were removed and the volume decreased in a vacuum centrifuge to approximately one fifth of the initial volume. The resulting concentrates were filtered through sterile non-pyrogenic filters (0.22 mm) and stored at −70° C. prior to testing. The concentrations of each extract were expressed as dry weight of original material to each ml of culture medium.

Induction was measured according to published methods (Tawfiq, N., Heaney, R. K., Plumb, J. A., Fenwick, G. R., Musk, S. R. R., & Williamson, G. (1995) Carcinogenesis 16, 1191–1194., Prochaska, H. J., & Santamaria, A. B. (1988) Anal. Biochem. 169, 328–336., Williamson, G., Plumb, G. W., Uda, Y., Price, K. R., & Rhodes, M. J. C. (1996) Carcinogenesis 17, 2385–2387.) with the following modifications. Each sample was analysed at eight concentrations using four replicates for each concentration. b-Napthoflavone was used as a positive control at a concentration of 0.2 mM. This typically produced a three-fold induction (CD; 0.02 mM) and was comparable to previous determinations. Each cultivar/hybrid was extracted on three occasions and analysed separately.

Non-volatile and volatile components of the hydrolytic breakdown products of the cultivars, wild species and the hybrids were analysed by GC-MS using a HP Chemstation GP800A equipped with a 30 m×0.25 mm HP1 crosslinked methylsilane column (Hewlett Packard Co. Palo Alto, Calif. USA). Typically, the column was heated from +60° C. to +250° C. at 20° C./min and mass spectra scanned from 35 to 250 m/z. Approximately 0.1 g of free-dried material was moistened with water, mixed thoroughly and incubated for 1 hr with occasional mixing. Non-volatile hydrolytic products were extracted from the samples with methylene chloride and filtered prior to analysis. in order to analyse volatile products, freeze-dried material (0.1 g) was moistened with water (0.5 ml), the glass vial sealed immediately and volatile products collected from the vial headspace with a solid phase matrix extraction (SPME) probe (Supelco Inc., Bellefonte, Pa., USA).

EXAMPLE 2

Glucosinolate Content of the Brassica Lines

Table 1 below shows the glucosinolate content of commercial broccoli cultivars Green Comet, Marathon and Trixie, wild B. oleracea species and hybrids between a doubled haploid line of the commercial cultivar Green Duke and wild Brassica species.

TABLE 1

Individual and total aliphatic glucosinolate content (μmoles/g dry weight ± 1 standard error) of broccoli cultivars, wild Brassica species and hybrids produced from crosses between GD DH and the wild Brasssica species.

|  | MSP* | MSB | PROP | BUT | MTP | OH-BUT | TOTAL |
|---|---|---|---|---|---|---|---|
| Green Comet | 0.1 ± 0.1 | 0.8 ± 0.5 | 0.2 ± 0.1 | 0.0 | 2.7 ± 0.5 | 0.5 ± 0.3 | 4.3 ± 0.5 |
| GD DH | 0.2 ± 0.2 | 4.6 ± 1.1 | 0.0 | 0.0 | 2.3 ± 0.6 | 0.0 | 7.1 ± 1.1 |
| Marathon | 1.0 ± 0.3 | 5.4 ± 1.1 | 0.2 ± 0.1 | 0.0 | 4.1 ± 0.7 | 0.0 | 10.7 ± 1.8 |
| Trixie | 0.4 ± 0.2 | 11.1 ± 2.1 | 0.2 ± 0.1 | 0.0 | 4.9 ± 1.2 | 0.0 | 16.6 ± 2.6 |
| B. atlantica | 0.9 ± 0.7 | 0.0 | 92.8 ± 25.4 | 0.5 ± 0.3 | 1.1 ± 1.0 | 0.0 | 95.3 ± 26.6 |
| B. drepanensis | 11.0 ± 1.7 | 0.0 | 0.0 | 0.0 | 51.6 ± 9.3 | 0.0 | 62.6 ± 10.9 |
| B. villosa | 119 ± 18 | 1.4 ± 0.2 | 0.0 | 0.1 ± 0.1 | 3.4 ± 0.9 | 0.1 ± 0.1 | 124 ± 19 |
| GD† × B. atlantica | 2.2 ± 0.8 | 5.3 ± 1.4 | 76.9 ± 20.8 | 23.6 ± 6.3 | 2.0 ± 0.7 | 43.7 ± 6.7 | 154 ± 30 |

TABLE 1-continued

Individual and total aliphatic glucosinolate content (μmoles/g dry weight ± 1 standard error) of broccoli cultivars, wild Brassica species and hybrids produced from crosses between GD DH and the wild Brasssica species.

|  | MSP* | MSB | PROP | BUT | MTP | OH-BUT | TOTAL |
|---|---|---|---|---|---|---|---|
| GD × B. drepanensis | 26.2 ± 2.9 | 76.5 ± 8.9 | 0.0 | 0.0 | 1.9 ± 0.4 | 0.0 | 105 ± 12 |
| GD × B. villosa | 26.4 ± 2.7 | 81.8 ± 5.0 | 0.0 | 0.0 | 1.0 ± 0.3 | 0.0 | 109 ± 7 |

*MSP: 3-methylsulfinylpropyl,
MSB: 4-methylsufinylbutyl,
PROP: 2-propenyl,
BUT: 3-butenyl,
MTP: 3-methylthiopropyl,
OH-BUT: 2-hydroxy-3-butenyl.
†GD: GD DH.

The level of 4-methylsulfinylbutyl glucosinolate in the broccoli cultivars were similar to those previously reported (Carlson, D. G., Daxenbichler, M. E., van Etten, C. H., Kwolek, W. F., & Williams, P. H. (1987) *J. Amer. Soc. Hort. Sci.* 112, 173–178.). Wild species had approximately a ten-fold greater level of total aliphatic glucosinolates than the cultivars, *B. villosa, B. drepanensis* and *B. atlantica* had predominantly 3-methylsulfinylpropyl, 3-methylthiopropyl and 2-propenyl glucosinolates. The differences in the glucosinolate profiles were attributed to differences in alleles at the GSL-OXID and GSL-ALK loci (Giamoustaris, A. & Mithen, R. (1996) *Theor. Appl. Genet.* 93, 1006–1010.). In the hybrids of [GD DH×*B. drepanensis*] and [GD DH×*B. villosa*] 4-methylaulfinylbutyl was the most abundant glucosinolate due to the dominant nature of the GSL-ELONG and GSL-OXID alleles found in GD DH and to the null GSL-ALK alleles in both parents. In the [GD DH×*B. atlantica*] hybrid, 3-butenyl glucosinolate was the predominant glucosinolate. 2-Hydroxy-3-butenyl glucosinolate was also present due to the action of a functional GSL-OH allele in the GD DH line (unpublished), which is not usually evident due to the null GSL-ALK allele preventing the biosynthesis of 3-butenyl glucosinolate.

EXAMPLE 3

Induction of Phase II Enzymes

Synthetic sulforaphane was used as a positive control to quantify induction of QR in Hepa 1c1c7 cells. It was a potent inducer and produced a three-fold induction at 1.6 mM (CD; 0.4 mM), comparable to previous determinations. No cytotoxicity was observed for any sample at any of the concentrations tested. Extracts from all the cultivars were poor inducers over the concentration range 0.001 mg/ml to 0.125 mg/ml. However, the induction was less than expected if 100% of the glucosinolates had been converted to isothiocyanates, and not to other products such as thiocyanate or nitrile derivatives (Fenwick, G. R., Heaney, R. K., & Mullin, W. J. (1983) *Crit. Rev. Food Sci. Nutr.* 18, 123–201).

For example, Marathon contained 5.4 mmoles of 4-methylsulfinylbutyl glucosinolate/g dry weight (Table 1). Therefore, an extract containing 75 mg/ml of Marathon would be expected to have a 4-methylsulfinylbutyl isothiocyanate concentration of 0.4 mM which would result in a two-fold induction. However, no significant induction was observed at this concentration. Indeed, 2.5 mg/ml of Marathon extract was required for a two-fold induction, which if 100% of the glucosinolate is converted to isothiocyanate, is equivalent to 13.5 mM 4-methylsulfinylbutyl isothiocyanate. Thus, either a small proportion of the glucosinolate had been converted to 4-methylsulfinylbutyl isothiocyanate, or the induction of QR activity was reduced by other components in the vegetable extract.

Figure 2:
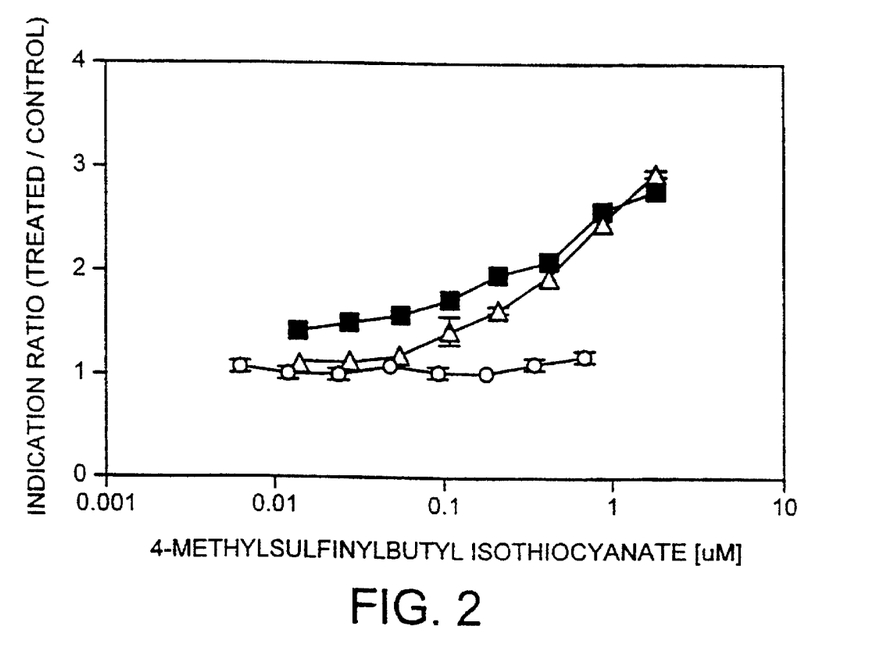
FIG. 2. Induction of QR activity (phase II enzymes) in murine hepatoma Hepa 1c1c7 cells using extracts from the cultivar Marathon and synthetic sulforaphane (4-methylsulfinylbutyl isothiocyanate).

To test for the presence of an inhibitor, Marathon extract (0.125 mg/ml) was spiked with synthetic sulforaphane prior to application to the Hepa 1c1c7 cells. The induction observed was similar to that of pure sulforaphane alone (FIG. 2), which demonstrated that there had been no inhibitory effect by other components in the extracts. In FIG. 2, the induction of QR in Hepa 1c1c7 cells using Sulforaphane (Δ); Marathon extract (0.125 mg/ml) with added sulforaphane (■) or Marathon extract (0.001 mg/ml to 0.125 mg/ml), (○), is shown. The estimated isothiocyanate concentration of the Marathon extract has been based on an assumption that 100% of the parent glucosinolate is converted to the isothiocyanate. Thus, Marathon extract (1 mg/ml) is equivalent to 5.4 uM 4-methylsulfinylbutyl isothiocyanate. Results for Marathon (0.125 mg/ml) with added sulforaphane have been plotted with respect to the added synthetic sulforaphane concentration only, as the Marathon extract alone has no significant effect on induction activity. Therefore, it is possible in Marathon (and also other cultivars) that only a proportion of the glucosinolate had been converted to the isothiocyanate.

Figure 3:
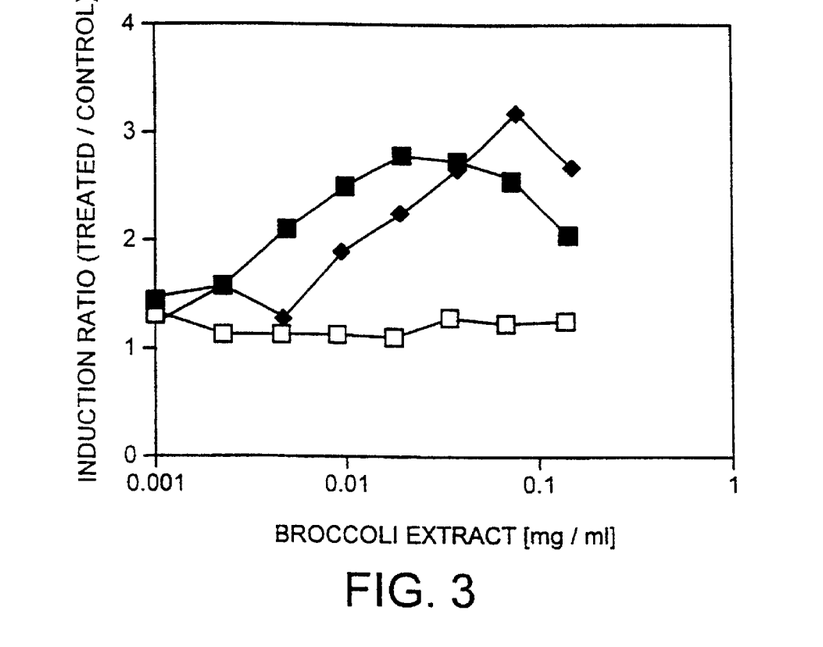
FIG. 3. Effect of extracts of *B. drepanensis; B. villosa;* and *B. atlantica* on induction of QR (phase II enzymes) in murine hepatoma Hepa 1c1c7 cells.

Extracts of *B. villosa* and *B. drepanensis* were potent inducers of QR activity. In contrast, extracts of *B. atlantica* did not induce QR activity, despite the high glucosinolate content (FIG. 3). In FIG. 3, the effects of the extracts of: *B. drepanensis* (■); *B. villosa* (♦); and *B. atlantica* (□) on the induction of QR in murine hepatoma Hepa 1c1c7 cells is shown. If it is assumed that 100% of the glucosinolate in these taxa had been converted to the isothiocyanate and not to other possible hydrolytic breakdown products (thiocyanate and nitrile derivatives), the apparent CD values for 3-methylthiopropyl isothiocyanate and 3-methylsulfinylpropyl isothiocyanate are 1.6 mM and 0.5 mM respectively. These values are both lower than those reported for synthetic isothiocyanates of 3.5 mM and 2.4 mM, as illustrated in Table 2. Indeed, if less of the glucosinolates had been converted to isothiocyanates the apparent CD values would be even lower. Table 2 below illustrates the induction of QR activity (phase II enzymes) in Hepa 1c1c7 cells by vegetable extracts.

TABLE 2

Potency of induction of QR in murine Hepa 1c1c7 cells by vegetable extracts.

|  | Predominant Isothiocyanate | Apparent CD value* ($\mu$M) | CD value for synthetic isothiocyanate ($\mu$M) (See Zhang (2)) |
|---|---|---|---|
| B. drepanensis | 3-methylthiopropyl | 1.6† | 3.5 |
| B. villosa | 3-methylsulfinylpropyl | 0.5† | 2.4 |
| GD‡ × B. drepanensis | 4-methylsulfinylbutyl | 0.3† | 0.4–0.8 |
| GD × B. villosa | 4-methylsulfinylbutyl | 0.3† | 0.4–0.8 |
| Synthetic sulforaphane | 4-methylsulfinylbutyl | 0.3 | 0.4–0.8§ |

*CD value: Concentration of parent glucosinolate required to double the induction activity of QR.
†Values quoted were calculated assuming 100% conversion of the parent glucosinolates to the corresponding isothiocyanate.
‡GD: GD DH.
§Other studies have quoted a CD value of 0.2 $\mu$M. See Prochaska (10).

The difference in potency could be due to either chemical differences between natural and synthetic isothiocyanates (e.g. nature of stereoisomers) or to other factors in the plant extracts which may include synergistic effects of low levels of other isothiocyanates. The lack of activity of extracts from B. atlantica emphasizes the importance of the structure of the glucosinolate side chain.

Figure 4:
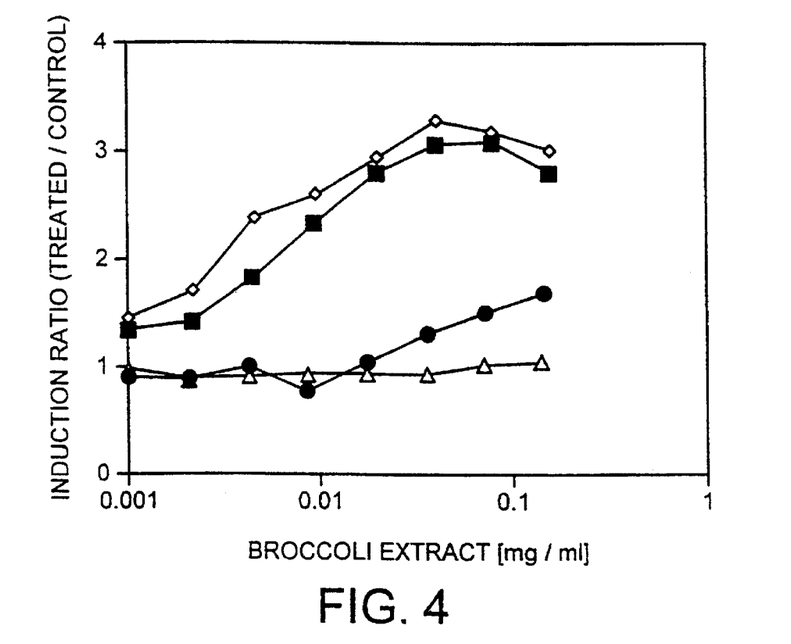
FIG. 4. The effect of extracts of the cultivar GD DH and the hybrids recovered from crosses with wild species [GD DH×*B. drepanensis*]; [GD DH×*B. villosa*]; and [GD DH×*B. atlantica*]; on the induction of QR (phase II enzymes) in murine hepatoma Hepa 1c1c7 cells.
Figure 5A:
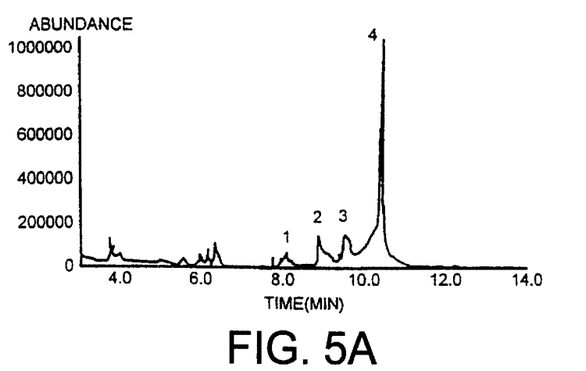
FIGS. 5A–5E Gas chromatograph profiles of the glucosinolates from an extract from a hybrid [GD DH×*B. drepanensis*].
Figure 5B:
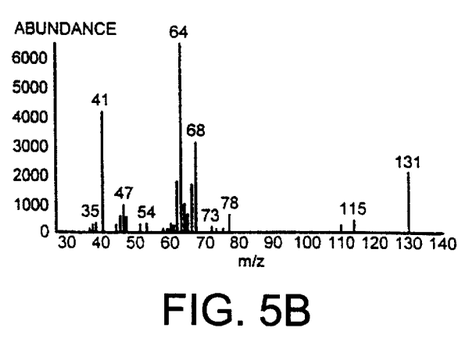
Figure 5C:
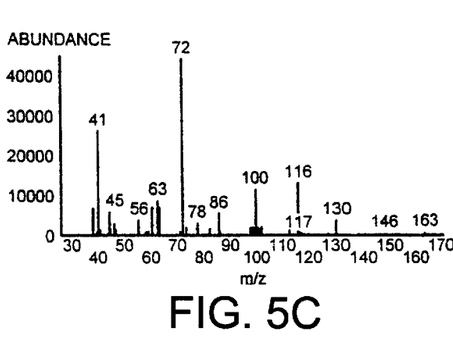
Figure 5D:
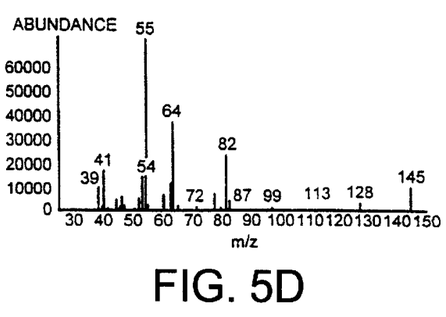
Figure 5E:
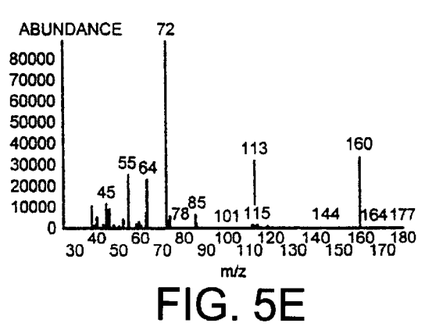

Extracts from both [GD DH×B. villosa] and [GD DH×B. drepanensis] were potent inducers of QR activity (FIG. 4). In FIG. 4, the effect of extracts of the cultivar GD DH (●); and the hybrid crosses [GD DH×B. drepanensis] (♦); [GD DH×B. villosa] (◇); and [GD DH×B. atlantica] (Δ); on the induction of QR in murine hepatoma Hepa 1c1c7 cells is shown. Based on 100% conversion of the glucosinolates to isothiocyanates, the apparent CD values of both extracts were 0.3 mM (4-methylsulfinylbutyl glucosinolate equivalent), which is similar to that of pure sulforaphane (above) and to that reported in previous studies. Thus, while there was an approximate ten-fold increase in the levels of 4-methylsulfinylbutyl glucosinolate in [GD DH×B. villosa] and [GD DH×B. drepanensis] compared to Marathon and GD DH, there was more than a 100-fold difference in ability to induce QR activity (i.e. it requires at least one hundred times the amount of Marathon tissue to induce equivalent QR activity compared to the GD DH hybrids).

In order to examine the composition and nature of the hydrolytic products, extracts were analysed by GC-MS (FIGS. 5A–5E). In FIGS. 5A–5E, gas chromatograph profiles of an extract from [GD DH×B. drepanensis] are shown. Mass spectrometry confirmed the peaks as (1), 3-methylsulfinylpropyl nitrile; (2), 4-methylsulfinylbutyl nitrile; (3), 3-methylsulfinylpropyl isothiocyanate; (4), 4-methylsulfinylbutyl isothiocyanate. Hydration of freeze-dried leaves of B. drepanensis and B. atlantica led to the production of large amounts of volatile 3-methylthiopropyl and 2-propenyl isothiocyanates. 3-Methylsulfinylpropyl isothiocyanate was detected in methylene chloride extracts from B. villosa, which was consistent with the glucosinolate profiles. In extracts of [GD DH×B. villosa] and [GD DH×B. drepanensis], the dominant isothiocyanate was 4-methylsulfinylbutyl isothiocyanate as expected. Relatively low levels of 3-methylsulfinylpropyl isothiocyanate and nitrile derivatives were also detected. In contrast, only trace amounts of 4-methylsulfinylbutyl isothiocyanate were detected in the cultivars. This indicated that the 100-fold difference in ability to induce QR activity between the two hybrids and the cultivars is due to both the increase in 4-methylsulfinylbutyl glucosinolate and to a greater conversion to the isothiocyanate.

What is claimed is:

1. A method for the production of *Brassica oleracea* with elevated levels of 4-methylsulfinylbutyl glucosinolates, or 3-methylsulfinylpropyl glucosinolates, or both, which comprises:
   (a) crossing a wild Brassica species selected from the group consisting of *B. villosa* and *B. drepanensis* with a *Brassica oleracea* breeding line to produce hybrid plants; and
   (b) selecting the hybrid plants of step (a) with levels of 4-methylsulfinylbutyl glucosinolates, or 3-methylsulfinylpropyl glucosinolates, or both, elevated above that initially found in the *Brassica oleracea* breeding line.

2. A method for the production of *Brassica oleracea* with levels of 4-methylsulfinylbutyl glucosinolates, or 3-methylsulfinylpropyl glucosinolates, or both, elevated above that initially found in *Brassica oleracea* breeding lines, which comprises:
   (a) crossing a wild Brassica species selected from the group consisting of *B. villosa* and *B. drepanensis* with a broccoli breeding line to produce hybrid plants;
   (b) selecting the hybrid plants of step (a) with elevated levels of 4-methylsulfinylbutyl glucosinolates, or 3-methylsulfinylpropyl glucosinolates, or both;
   (c) backcrossing to a broccoli breeding line to produce backcrossed plants; and
   (d) selecting the backcrossed plants of step (c) with elevated levels of 4-methylsulfinylbutyl glucosinolates, or 3-methylsulfinylpropyl glucosinolates, or both.

3. The method according to claim 2 which additionally comprises:
   (e) selecting a broccoli line with elevated levels of 4-methylsulfinylbutyl glucosinolates, or 3-methylsulfinylpropyl glucosinolates, or both, capable of causing a strong induction of phase II enzymes.

4. A method for the production of *Brassica oleracea* with levels of 4-methylsulfinylbutyl glucosinolates, or 3-methylsulfinylpropyl glucosinolates, or both, elevated above that initially found in *Brassica oleracea* breeding lines, and comprising SI alleles, the presence of which in *Brassica oleracea* results in self-incompatibility of the *Brassica oleracea*, the method comprising:
   (a) crossing a wild Brassica species selected from the group consisting of *B. villosa* and *B. drepanensis* with a broccoli double haploid breeding line containing the SI alleles to produce hybrid plants;
   (b) selecting the hybrid plants of step (a) with elevated levels of 4-methylsulfinylbutyl glucosinolates, or 3-methylsulfinylpropyl glucosinolates, or both;
   (c) screening the hybrid plants of step (b) for the SI alleles with RFLP markers to identify the hybrid plants comprising the SI alleles; and
   (d) selecting the hybrid plants identified in step (c).

5. The method according to claim 4, additionally comprising: backcrossing the plant of step 4(b) to the brocoli breeding line and selecting backcrossed plants; with elevated levels of 4-methylsulfinylbutyl glucosinolates, or 3-methylsulfinylpropyl glucosinolates, or both; and
   (e) selecting a broccoli line with elevated levels of 4-methylsulfinylbutyl glucosinolates, or 3-methylsulfinylpropyl glucosinolates, or both, and SI alleles, which is capable of causing a strong induction of phase II enzymes.

6. A method for the production of *Brassica oleracea* with levels of 4-methylsulfinylbutyl glucosinolates, or 3-methylsulfinylpropyl glucosinolates, or both, elevated above that initially found in *Brassica oleracea* breeding lines, which comprises:
 (a) crossing a wild Brassica species selected from the group consisting of *B. villosa* and *B. drepanensis* with a broccoli double haploid breeding line to produce hybrid plants;
 (b) using DNA probes to select the hybrid plants of step (a) with a genetic combination encoding expression of elevated levels of 4-methylsulfinylbutyl glucosinolates, or 3-methylsulfinylpropyl glucosinolates, or both;
 (c) backcrossing to the broccoli double haploid breeding line to produce backcrossed plants;
 (d) selecting the backcrossed plants of step (c) with the genetic combination encoding the expression of elevated levels of 4-methylsulfinylbutyl glucosinolates, or 3-methylsulfinylpropyl glucosinolates, or both; and
 (e) selecting a broccoli line with elevated levels of 4-methylsulfinylbutyl glucosinolates, or 3-methylsulfinylpropyl glucosinolates, or both, capable of causing a strong induction of phase II enzymes.

7. The method according to claim 1, wherein only 4-methylsulfinylbutyl glucosinolate is elevated.

8. The method according to any one of claim 1, wherein only 3-methylsulfinylpropyl glucosinolate is elevated.

9. An edible *Brassica oleracea* plant produced according to the method of claim 1.

10. An edible portion of a broccoli plant produced according to the method of claim 1.

11. Seed of a broccoli plant produced according to the method of claim 1.

12. The method according to claim 6 where the DNA probes used are selected from the group consisting of: pW176, pW141, pW207, pW224, pW114, pW145, pW123, pW138, pW197, pW228 and pW106.

13. A broccoli plant having elevated levels of 3-methylsulfinylpropyl glucosinolates, or 4-methylsulfinylbutyl glucosinolates, or both, elevated above that initially found in *Brassica oleracea* breeding lines, wherein the broccoli plant is a hybrid plant produced by crossing a broccoli breeding line with a wild Brassica species selected from the group consisting of *B. drepanensis* and *B. villosa*.

14. The broccoli plant according to claim 13, wherein the concentration of 3-methylsulfinylpropyl glucosinolates, or 4-methylsulfinylbutyl glucosinolates, or both, is between 10 and 100 μmoles per gram of dry weight.

15. A broccoli inflorescence having elevated levels of 3-methylsulfinylpropyl glucosinolates, or 4-methylsulfinylbutyl glucosinolates, or both, elevated above that initially found in *Brassica oleracea* breeding lines, wherein the broccoli inflorescence is obtained from a hybrid plant produced by crossing a broccoli breeding line with a wild Brassica species selected from the group consisting of *B. drepanensis* and *B. villosa*.

16. The broccoli inflorescence according to claim 15, wherein the concentration of 3-methylsulfinylpropyl glucosinolates, or 4-methylsulfinylbutyl glucosinolates, or both, is between 10 and 100 μmoles per gram of dry weight.

17. A Brassica plant cell having levels of 3-methylsulfinylpropyl glucosinolates, or 4-methylsulfinylbutyl glucosinolates, or both, elevated above that initially found in *Brassica oleracea* breeding lines, wherein the cell is a cell of a hybrid plant produced by crossing a broccoli breeding line with a wild Brassica species selected from the group consisting of *B. drepanensis* and *B. villosa*.

18. The plant cell according to claim 17, wherein the cell is an inflorescence cell.

19. The plant cell according to claim 17, wherein the concentration of 3-methylsulfinylpropyl glucosinolates, or 4-methylsulfinylbutyl glucosinolates, or both, is, between 10 and 100 μmoles per gram of dry weight.

* * * * *

UNITED STATES PATENT AND TRADEMARK OFFICE
CERTIFICATE OF CORRECTION

PATENT NO. : 6,340,784 B1
DATED : January 22, 2002
INVENTOR(S) : Mithen et al.

It is certified that error appears in the above-identified patent and that said Letters Patent is hereby corrected as shown below:

Title page,
Item [75], Inventor, "Gary Williamson" should be removed.

Column 2,
Line 55, "3-methylaulfinylpropyl" should read -- 3-methylsulfinylpropyl --;

Column 6,
Line 14, "RPLP" should read -- RFLP --;

Column 7,
Line 54, "RPLP" should read -- RFLP --;

Column 8,
Line 29, "4-methylaulfinylbutyl" should read -- 4-methylsulfinylbutyl --;

Column 9,
Line 52, "Lo" should read -- to --;

Column 11,
Line 5, "3-methylaulfinylpropyl" should read -- 3-methylsulfinylpropyl --;
Line 27, "cultivate" should read -- cultivars --;

Column 17,
Line 25, delete "any one of".

Signed and Sealed this

Twenty-seventh Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,340,784 B1
DATED : January 22, 2002
INVENTOR(S) : Richard Mithen et al.

It is certified that error appears in the above-identified patent and that said Letters Patent is hereby corrected as shown below:

Column 8,
Line 63, wherein "...and/or 3-methylaulfinylpropyl" should read
-- ...and/or 3-methylsulfinylpropyl... --.

Signed and Sealed this

Eighteenth Day of January, 2005

JON W. DUDAS
*Director of the United States Patent and Trademark Office*